United States Patent [19]

Kyle et al.

[11] Patent Number: 5,711,983
[45] Date of Patent: Jan. 27, 1998

[54] DINOFLAGELLATE BIOMASS, METHODS FOR ITS PRODUCTION, AND COMPOSITIONS CONTAINING THE SAME

[75] Inventors: David John Kyle, Catonsville; Sue Ellen Reeb; Valerie Jacqueline Sicotte, both of Baltimore, all of Md.

[73] Assignee: Martek Biosciences Corporation, Columbia, Md.

[21] Appl. No.: 583,845

[22] Filed: Jan. 11, 1996

Related U.S. Application Data

[62] Division of Ser. No. 386,079, Feb. 9, 1995, Pat. No. 5,492,938, which is a division of Ser. No. 916,874, filed as PCT/US91/00733 Feb. 4, 1991, Pat. No. 5,397,591, which is a continuation-in-part of Ser. No. 479,135, Feb. 13, 1990, Pat. No. 5,407,957.

[51] Int. Cl.$^6$ ............................ A23K 1/00; A23K 1/18; C12N 1/12
[52] U.S. Cl. .................... 426/635; 426/805; 435/257.1
[58] Field of Search ............................. 426/635, 805; 435/257.1

[56] References Cited

U.S. PATENT DOCUMENTS

| | | | |
|---|---|---|---|
| 3,458,625 | 7/1969 | Ensor et al. | 424/523 |
| 3,854,240 | 12/1974 | Oldham et al. | 47/1.4 |
| 4,485,173 | 11/1984 | Giehart | 435/134 |
| 4,513,008 | 4/1985 | Recivi et al. | 514/560 |
| 4,526,902 | 7/1985 | Rubin | 514/560 |
| 4,670,285 | 6/1987 | Clandinin et al. | 426/602 |
| 4,681,896 | 7/1987 | Horrobin | 514/552 |
| 4,710,383 | 12/1987 | Dick | 424/449 |
| 4,752,618 | 6/1988 | Mascioli et al. | 514/549 |
| 4,753,964 | 6/1988 | Horribin | 514/558 |
| 4,775,749 | 10/1988 | Hijiya et al. | 536/103 |
| 4,780,456 | 10/1988 | Pistolesi et al. | 514/78 |
| 4,792,418 | 12/1988 | Rubin et al. | 554/186 |
| 4,826,877 | 5/1989 | Stewart et al. | 514/560 |
| 4,843,095 | 6/1989 | Rubin | 514/558 |
| 4,868,001 | 9/1989 | Maruta | 426/623 |
| 4,874,603 | 10/1989 | Fratzer | 514/458 |
| 4,874,629 | 10/1989 | Chang et al. | 426/601 |
| 4,911,944 | 3/1990 | Holub | 426/635 |
| 4,960,795 | 10/1990 | Salte et al. | 514/560 |
| 4,963,385 | 10/1990 | Antrim et al. | 426/602 |
| 5,013,569 | 5/1991 | Rubin | 426/585 |
| 5,116,624 | 5/1992 | Horrobin et al. | 514/560 |
| 5,116,871 | 5/1992 | Horrobin et al. | 514/560 |
| 5,120,760 | 6/1992 | Horrobin | 514/458 |
| 5,130,242 | 7/1992 | Barclay | 435/134 |

FOREIGN PATENT DOCUMENTS

| | | |
|---|---|---|
| 231 904 | 8/1987 | European Pat. Off. |
| 276 982 | 8/1988 | European Pat. Off. |
| 342 795 | 11/1989 | European Pat. Off. |
| 404 058 | 12/1990 | European Pat. Off. |
| 459 744 | 4/1991 | European Pat. Off. |
| 3 603 00 | 8/1987 | Germany |
| 63/295 527 | 12/1988 | Japan |
| 61/080 250 | 3/1989 | Japan |
| 01/196 255 | 8/1989 | Japan |
| 01/215 245 | 8/1989 | Japan |
| 01/279 827 | 11/1989 | Japan |
| 01/279 830 | 11/1989 | Japan |
| 01/290 625 | 11/1989 | Japan |
| 02/013 388 | 1/1990 | Japan |
| 02/49723 | 2/1990 | Japan |
| 02/257 835 | 10/1990 | Japan |
| 2 061 881 | 1/1989 | United Kingdom |
| 89/00606 | 1/1989 | WIPO |
| WO 90/12858 | 11/1990 | WIPO |
| WO 90/13656 | 11/1990 | WIPO |
| WO 91/07498 | 5/1991 | WIPO |

OTHER PUBLICATIONS

Cox, "Dinoflagellates," *CRC Handbook of Microbiol.*, vol. II, pp. 489–501.

Sorokin, et al., 1958, *The Natural Environment Res. Council.*

Haskins, et al., 1964, "Steroids and The Stimulation of Sexual Reproduction of a Species of Pythium," *Can. J. Microbiol.*, 10:187–195.

Gold, et al., 1966, "Growth Requirements of *Fyrodinium cohnii*," *Protozool.*, 13:255–257.

Tyrell, D., 1967, "The Fatty Acid Compositions of 17 Entomophthora Isolates," *Can. J. Microbiol.*, 13:755–760.

Ackman, et al., 1968, "Marine Phytoplankter Fatty Acids," *J. Fish Res. Bd. Can.*, 25:1603–1620.

Harrington, et al., 1970, "The Polyunsaturated Fatty Acids of Marine Dinoflagellates," *J. Protozool.*, 17:213–219.

Beach, et al., 1973, "Environmental Influences on the Docosahexaenoiate Content of the Triacylglycerols and Phosphatidycholine of a Heterotrophic, Marine Dinoflagellate, *Crypthecodinium cohnii*," *B.B.A.*, 316:56–65.

Ervin, 1973, "Comparative Biochemistry of Fatty Acids in Eukaryotic Microorganisms," *Lipids and Biomembrane of Eukaryotic Microorganisms*, Chap. 2, pp. 41–143, Acad. Press.

Orcutt, et al., 1974, "Effect of Light Intensity upon Lipid Composition of *Nitzschia closerium (Cylindrotheca fusiformis)*," *Lipids*, 9:1000–1002.

(List continued on next page.)

*Primary Examiner*—John P. Weber
*Attorney, Agent, or Firm*—Baker & Botts, L.L.P.

[57] ABSTRACT

A biomass is provided which consists essentially of cells of dinoflagellates of the class Dinophyceae which have been cultivated to produce high cell mass and high DHA content. Biomass consisting of cells of *Crypthecodinium cohnii* is preferred. The cells are cultivated in an aerobic fermentor to achieve a cell density of a least 10 grams biomass per liter of nutrient solution by maintaining in the fermentor a dissolved oxygen level of at least about 10% of air saturation, and by inducing a stationary phase with a limiting nitrogen source in the nutrient solution. Under these conditions a single cell oil which contains at least 20% docosahexaenoic acid (DHA) in the triglyceride form at a concentration of at least about 1.5 grams per liter of nutrient solution is produced in the biomass. The biomass is suitable as an aquaculture feed.

10 Claims, 2 Drawing Sheets

OTHER PUBLICATIONS

Beach, et al., 1974, "Biosynthesis of Oleic Acid and Docosahexanoic Acid by a Heterotrophic Marine Dinoflagellate *Crypthecodinium cohnii*," *Biochim. Biophys. Acta*, 369:16–24.

Matuchka, M., 1975, "Higher Fatty Acids in Chlorella Vulgaris (Pyre–Noidosa): Content of Individual Acids and Use of the Algae for the Preparation of Higher Fatty Acids," *Radioisotopy*, 15:205–214.

Tuttle, et al., 1975, "An Optimal Growth Medium for the Dinoflagellate *Crypthecodinium cohnii*," *Phycologia*, 14:(1) pp. 1–8.

Guillard, Robt., 1975, "Culture of Phytoplankton For Feeding Marine Invertebrates,"in *Culture of Marine Invertebrae Animals*, Smith, et al., eds.

Caspary, Wolfgang F., 1978, "Breath Tests," *Clinics in Gastroenterol.*, 7:351–374.

Pohl, et al., 1979 "Fatty Acids and Lipids of Marine Algae and the Control of Their Biosynthesis by Environmental Factors," *Marine Algae in Pharmaceutical Science*, pp. 473–523, Hoppe, et al., eds.

Aaronson, et al., 1980, "Microalgae as a Source of Chemicals and Natural Products," *Algae Biomass*, pp. 575–601, Shelef, et al., eds.

Pohl, 1981, *CRC Handbook of Biosolar Res.*, Mitsui, et al., eds. pp. 383–404, Fla., CRC Press.

Sonnenborn, et al., 1982, "Purification and Properties of the Fatty Acid Synthetase Complex From the Marine Dinoflagellate, *Crypthecodinium cohnii*, " *Biochim. Biopyhs. Acta*, 712:523–534.

Kame, et al., 1983, "Use of Fish Oil Fatty Acids (EPA and DHA) in Nutrition–Supplementing Foods and in Drugs," *Yushi*, 36:86–92 (Abst. only) (C.A. 100, 66638d).

Guillard, et al., 1984, "Culturing Dinoflagellates," in *Dinoflagellates*, Spector, ed., Chap. 12, pp. 391–442, Acad. Press.

Tornabene, 1983 "Lipid Composition of the Nitrogen Starved Green Algae *Neochloris oleoabundans*," *Enzyme Microb. Technol.*, 5.

Loeblich, III, A.R., 1984, "Dinoflagellate Physiology & Biochemistry," in *Dinoflagellates*, Chap. 9, pp. 304–305, Spector, D.L., ed.

Ben–Amotz., 1985, "Chemical Profile of Selected Species of Microalgae With Emphasis on Lipids," *J, Phycol.*, 21:72–81.

Lands, 1986, *Fish & Human Hlth.*, Acad. Press.

Ratledge, 1986, "The Potential of Microorganisms for Oil Production—A Review of Recent Publications," *AOCS, (World Conference)*.

Crawford, M.A., 1987, "The Requirements of Long Chain n–6 and n–3 Fatty Acids for the Brain," in *Proc. AOCS Conf., Short Course on Polyunsaturated Fatty Acids and Eicosanoids*, Chap. 33, pp. 270–295, Lands, W.E.M. ed., American Oil Chemists' Soc.

Liu, et al., 1987, "Increase in Plasma Phospholipid Doconsahexanoic and Eicosapentaenoic Acids as a Reflection of Their Intake and Mode of Administration," *Pedatr. Res.*, 22:292–296 (Abst. Only).

Hansson, et al., 1988, "Effect of Culture Conditions on Mycelial Growth and Production of gamma (?)–Linolenic Acid by the Fungus *Mortierella ramanniana*," *Appl. Microbiol. Biotechnol.*, 28:240–246.

Henderson, et al., 1988, "Lipid Composition and Biosynthesis in the Marine Dinoflagellate *Crypthecodinium cohnii*," *Phytochem.*, 27:1679–1683.

Yongmanitchai, et al., 1989, "Omega–3 Fatty Acids: Alternative Sources of Production," (title partially obliterated) *Process Biochem.*, 24:117–125.

Kyle, et al., 1989, "Microalgae as a Source of EPA," *Proc. Int. Symp. Diet. Lipids, Benefits, Hazards, and Use*, Novotel, Goteborg, Sweden pp. 161–169.

Ackman, R.G., 1989, "Problems in Fish Oils and Concentrates," in *Fats For The Future*, Chap. 13, pp. 189–200, Cambie, ed.

Innis, et al., 1990, "Plasma and Red Blood Cell Fatty Acids of Low–Birth–Weight Infants Fed Their Mother's Expressed Breast Milk or Preterm–Infant Formula," *Am. J. of Clin. Nutri.*, 51:994–1000.

Noguchi, et al., 1991, "Feeds Containing Highly Unsaturated Fatty Acids and Vitamin E for Swine and Production of Pork Using the Feeds," (C.A. 114, 41472 w).

Kyle, 1991, *Adv. Applied Biotech.*, 12.

Hinden, Wash, Post, 1994 Jan. 24, Business p. 29.

Sanders, et al., 1978, "Studies of Vegans: The Fatty Acid Composition of Plasma Choline Phosphoglycerides, Erthrocytes, Adipose Tissue, and Breast Milk, and some Indicators of Susceptibility to Ischemic Heart Disease in Vegans and Omnivore Controls," *Am. J. Clin. Nutri.*, 31:805–813.

Shifrin, et al., 1980, "Phytoplankton Lipids: Environmental Influences on Production and Possible Commercial Applications," *Algae Biomass*, pp. 627–645, Shelef, et al., eds.

Shifrin, 1984, "Oils From Microalgae," in *Biotech. for Oils & Fats Indust.*, Chap. 14, pp. 145–162, Ratledge, et al., eds.

Neuringer, et al., 1986, "Biochemical and Functional Effects of Prenatal and Postnatal $\omega3$ Fatty Acid Deficiency on Retina and Brain in Rhesus Monkeys," *Proc. Natl. Acad. Sci. U.S.A.*, 83:4021–4023.

Bazan, et al., 1986, "Decreased Content of Docosahexaenoate and Arachidonate in Plasma Phospholipids in Usher's Syndrome," *Biochem. Biophys, Res. Comm.*, 141:600–604.

El Boustani, et al., 1987, "Enteral Absorption in Man of Eicosapentaenoic Acid in Different Chemical Forms," *Lipids*, 22:711–714.

Puppione, et al., 1988, "Marine Mammals Animal Models for Studying the Digestion and Transport of Dietary Fats Enriched in $\omega$–3 Fatty Acids. Positional Analyses of Milk Fat Triacylglycerol Molecules," in *Dietary $\omega$–3 and $\omega$–6 Fatty Acids*, Galli, et al., eds., Plenum Press.

Weaver, et al., 1989, "The Effect of Placement of EPA in Ingested Triglyceride on EPA Accumulation in Human Platelet and Plasma Phospholipids, " in *Health Effects of Fish and Fish Oils*, Clandra, ed., St. John's, Newfoundland.

Martinez, M. 1989, "Changes in the Polyunsaturated Fatty Acid Profiles in Zellweger Syndrome Suggesting a New Enzymatic Defect: Delta–4 Desaturase Deficiency," in *Dietary $\omega3$ and $\omega6$ Fatty Acids*, C.Galli, et al., eds., Plenum Press.

Miller, et al., 1989 "Guinea Pig Epidermis Generates Putative Anti–Inflammatory Metabolites from Fish Oil Polyunsaturated Fatty Acids," *Lipids*, 24:998–1003.

Vaddadi, et al., 1989, "A Double–Blind Trial of Essential Fatty Acid Supplementation if Patients With Tardive Dyskinesia," *Psychiatry Res.*, 27:313–323.

Yeh, et al., 1990, "Enrichment of (n–3) Fatty Acids of Suckling Rats by Maternal Dietary Menhaden Oil," *J. Nutr.*, 120 (C.A. 113, 39304d).

Soderberg, et al., 1990, "Fatty Acid Compositon of Brain Phospholipids in Aging and in Alzheimer's Disease," *Lipids*, 26:421–425.

Carlson, et al., 1990, "Long-Term Docosahexaenoate (DHA) and Eicosapentanoate (EPA) Supplementation of Preterm Infants: Effects on Biochemistry, Visual Acuity, Information Processing and Growth in Infancy," R3, 1990 Annual Meeting Abstracts.

Moore, et al., 1990, "Astrocytes, Not Neurons, Produce Docosahexaenoic Acid (22:3ω3) and Arachidonic Acid (20:4ω–6)," *J. Neurochem.*, pp. 518–524.

DINOFLAGELLATE BIOMASS, METHODS FOR ITS PRODUCTION, AND COMPOSITIONS CONTAINING THE SAME

This application is a division of application Ser. No. 08/386,079, filed Feb. 2, 1995, now U.S. Pat. No. 5,492,938, which is a division of application Ser. No. 07/916,874, filed Aug. 13, 1992, now U.S. Pat. No. 5,397,591, which is based on PCT/US91/00733, filed Feb. 4, 1991, which is a continuation-in-part of application Ser. No. 07/479,135, filed Feb. 13, 1990, now U.S. Pat. No. 5,407,957.

BACKGROUND OF THE INVENTION

This invention relates to edible, single-cell oil containing docosahexaenoic acid (DHA). The invention also relates to methods of producing such oil containing DHA in commercially viable yields and to products containing the oil.

DHA is an omega-3-fatty acid and is the most abundant long chain polyunsaturated fatty acid (PUFA) in the grey matter of the brain. Omega-3-fatty acids in general are known to be beneficial in reducing the incidence of coronary heart disease [Lands, *Fish and Human Health* (1986) Academic Press]. However, the metabolism of omega-3-fatty acids is not well understood. Thus, precise clinical dosages and efficacy remain unknown.

Cold water marine fish are a known source of omega-3-fatty acids, including DHA. U.S. Pat. No. 4,670,285 discloses the use of fish oil from fish such as menhaden and herring as a source of $C_{22}$ omega-3-fatty acids. Indeed, fish oils are the primary commercial source of omega-3-fatty acids. Often, however, fish oils are unusable for human consumption because of contamination with environmental pollutants such as PCB's.

There also are problems associated with the recovery of fish oils containing DHA for food uses. Such oils often have a fishy odor and unpleasant tastes associated with the oxidation products of the fatty acids. These tastes and toxicities of peroxides render the oils unsatisfactory for use in edible compositions such as baby food and infant formulas.

Marine microorganisms also are known to contain DHA. In particular, various species of dinoflagellates are known to contain DHA. Harrington et al., "The Polyunsaturated Fatty Acids of Marine Dinoflagellates" *J. Protozoal,* 17:213–219 (1970), characterize the fatty acid content of eight photosynthetic and one heterotrophic marine dinoflagellates, and conclude that the dinoflagellates are a primary producer group of docosahexaenoic acid and contribute substantial amounts of that compound to the marine food chain.

Successful cultivation of dinoflagellates to produce an edible oil containing DHA has not been achieved. Dinoflagellates in general are very slow growing and are shear sensitive. Guillard et al., *Dinoflagellates,* (1984) Academic Press. The prior art discloses that even a small amount of agitation in the culturing vessel reduces growth of the cultures. However, such agitation would be necessary to achieve adequate oxygenation in order to maximize growth for commercial production.

DHA is thought to be essential for the proper brain and vision development of infants because, as noted above, it is the most abundant long chain PUFA in the brain and retina. Although a metabolic pathway exists in mammals for the biosynthesis of DHA from dietary linolenic acid, this pathway is bioenergetically unfavorable [Crawford, P. AOCS. *Short Course in Polyunsaturated Fatty Acids and Eicosanoids,* pp. 270–295 (1987)] and mammals, like fish, are thought to obtain most of their DHA from dietary sources. In the case of infants, the most likely source would be human milk. Indeed, DHA is the most abundant C22 omega-3 PUFA in human milk. Generally, however, DHA is absent from infant formulas. U.S. Pat. No. 4,670,285 does disclose an infant formula containing omega-3-fatty acids. However, the acids utilized therein are obtained from egg or fish (Talapia) oil and have associated therewith the unpleasant characteristics previously described. Furthermore, fish oils generally contain another omega-3-fatty acid, eicosapentaenoic acid (EPA), an undesirable component in infant formulas because of its prolonged anticoagulant effects and its depression of arachidonic levels in infants. This has been correlated with reduced rates of infant weight gain (Carleson et al. INFORM 1:306.) Indeed, EPA levels are very low in human milk (less than one-forth that of DHA).

Accordingly, it is an object of the present invention to provide a single-cell edible oil containing DHA. Preferably this oil will have no significant quantities of other polyunsaturated fatty acids (PUFA's), i.e. greater than about 2% of the total fatty acid content. In general, it is an object of the present invention to produce single-cell oil in commercially viable yields. The oil, characterized herein as a "designer" oil, after extraction can be used in infant formulas, baby foods, dietary supplements and pharmaceuticals.

In addition, it would be desirable to acquire further knowledge of the metabolic pathway of omega-3-fatty acids. Isotopically labeled DHA would be of great utility in this regard. However, to date, no method has been known to produce abundant quantities of isotopically labeled DHA. Thus, it also is an object of the present invention to provide isotopically labeled DHA in sufficient quantities to undertake such research.

SUMMARY OF THE INVENTION

The present invention relates to the cultivation of microorganisms, notably dinoflagellates, in a fermentor, induction of those microorganisms to produce significant quantities of single cell oil containing a high proportion of DHA and recovery of that oil. As used herein, "single cell oil" refers to a lipid product of a unicellular organism. The present invention also includes mutant organisms capable of producing enhanced quantities of single-cell oil containing at least about 20% by weight DHA and includes single cell oil containing DHA.

The present invention provides an economical method of obtaining enhanced levels of edible oils containing DHA. Additionally, the method permits the commercial cultivation of dinoflagellates in elevated cell densities.

Edible oils produced by the method of this invention lack unpleasant tastes and fishy odors and also are free of environmental contaminants often found in DHA-containing oils from conventional sources. Accordingly, the present invention further includes food products containing the oil of this invention.

DETAILED DESCRIPTION OF THE BEST MODE OF PRACTICING THE INVENTION

Figure 1:
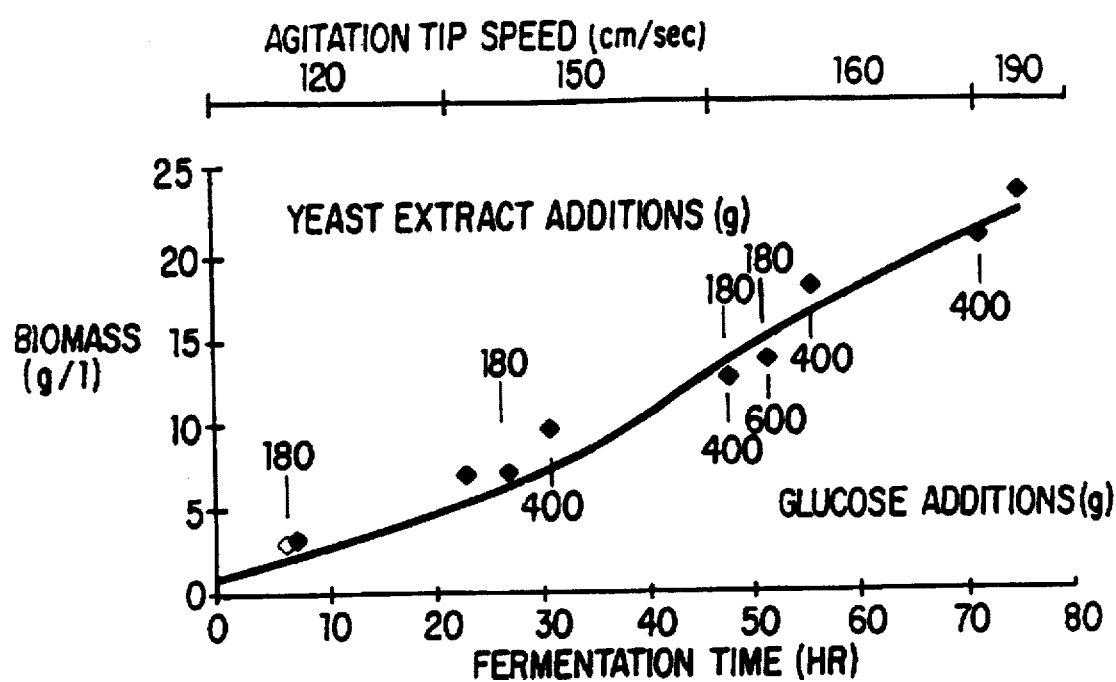
FIGS. 1, 2 and 3 are graphic illustrations of *C. cohnii* biomass accumulation over time with the addition of various nutrients.

In accordance with the present invention, microorganisms capable of producing a single cell oil containing DHA are cultivated in a fermentor in a nutrient solution capable of supporting the growth of such organisms. Preferably the single cell oil will contain at least about 20% by weight DHA.

Any microorganisms capable of producing a single-cell edible oil containing DHA can be used in the present invention. For example, photosynthetic diatoms can be used. Preferred microorganisms are marine dinoflagellates, including *Crypthecodinium sp*. Especially preferred is *Crypthecodinium cohnii*, an obligate heterotroph requiring a reduced carbon source for growth. *C. cohnii* is preferred because it contains a fatty acid profile in which DHA is the only PUFA present in sufficient quantities (greater than about 1% of the total amount of PUFAs). Samples of this organism, designated MK8840, have been deposited with the American Type Culture Collection at Rockville, Md., and assigned accession number 40750. As used herein, microorganism, or any specific type of microorganism, includes wild strains, mutants or recombinant types. Any microorganism which produces enhanced levels of oil containing DHA is considered to be within the scope of this invention. One of the features of the present invention is its recognition of the edible oil-producing capability of microorganisms such as dinoflagellates and the attendant solution to the problem of maintaining a reliable, economic source of such oils. Accordingly, wild-type and recombinant microorganisms designed to produce single cell oil containing DHA are an aspect of this invention. Such recombinant organisms would include those designed to produce greater quantities of DHA in the single cell oil, greater quantities of total oil, or both, as compared to the quantities produced by the same wild type microorganism, when provided with the same substrates. Also included would be microorganisms designed to efficiently use more cost-effective substrates while producing the same amount of single cell oil containing DHA as the comparable wild-type microorganism.

In general, those of skill in the art would not consider *C. cohnii* a suitable organism for cultivation in a fermentor. Previous workers have commented on the extremely complex mixture of nutrients required to successfully cultivate *C. cohnii*. Gold et al. *Protozoal*, 13:255–257 (1966); Guillard, et al. in "Dinoflagellates", Academic Press (1984); Henderson, et al., *Phytochemistry* 27:1679–1683 (1988). In contrast, the present invention achieves the cultivation of DHA-producing microorganisms in a simple medium containing glucose and yeast extract. Use of these components in a solution such as seawater provides economically significant growth rates and cell densities. For example, during the course of a 3–5 day fermentation, *C. cohnii* cell densities of at least 10 grams of biomass per liter of solution, and typically from 20 to about 40 grams per liter, can be attained. Such densities have not heretofore been attainable.

Although cultivation can occur in any suitable fermentor, preferably the organism is grown either in a stirred tank fermentor (STF) or in an air lift fermentor (ALF), both types known to those of skill in the art. When a STF is selected, agitation is provided using either Rushton-type high efficiency turbines or pitched-blade or marine impellers. Agitation and sparging renew the supply of oxygen to the microorganisms. The rate of agitation normally is increased as the biomass increases, due to the increased demand for oxygen. It is desirable to keep the tip speed at not greater than about 500 cm/sec, preferably not greater than about 300 cm/sec. Selection of strains of microorganisms which are capable of withstanding greater tip speeds without undergoing shear is within the purview of those of skill in the art. The use of such strains is expressly included in this invention.

As noted above, seawater is an acceptable medium for the nutrient solution. The seawater can be either natural, filtered or an artificial mix, each of which can be diluted to reduced salinities, such as ½ to ¼ normal strength, with tap water or concentrated to 2 times normal strength. A preferred example is Instant Ocean® (IO) brand artificial seawater. Although *C. cohnii* is a marine microorganism, some growth has been observed in zero salinity. The use of variants which grow well in reduced salinities is specifically encompassed by this invention. Micronutrients can be added and may be required at low salinities. However, such micronutrients are known to those of skill in the art and generally are present in seawater or tap water. If the organism selected is heterotrophic, such as *C. cohnii*, then a carbon source is added.

Preferably, after addition of the seawater medium to the fermentor, the fermentor containing the medium is sterilized and cooled prior to adding the nutrients and a seeding population of microorganism. (Although it is acceptable to sterilize the nutrients together with the seawater, sterilization in this manner can result in a loss of available glucose.) The nutrients and microorganism can be added simultaneously or sequentially.

An effective seed concentration can be determined by those of skill in the art. When a STF is used, the addition of a population of from about 0.05 to 1.0 grams of dry weight equivalent per liter at the beginning of the fermentation is preferred. This is about $10^6$ cells per ml. Thus, for a 30 liter fermentor, 1–3 liters of seeding media, containing viable cells at a density of 20 g dry weight per liter would be added.

Oxygen levels preferably are maintained at a D.O. of at least about 10% of air saturation level. Biosynthesis of DHA requires oxygen and, accordingly, higher yields of DHA require D.O. levels at from about 10% to 50% of air saturation levels. Agitation tip speeds of 150–200 cm/sec in combination with an aeration rate of 1 VVM (volume of air/volume of fermentor per minute) provides D.O. levels of from about 20% to about 30% at biomass densities of about 25 g dry weight/liter of culture. Higher cell densities may require higher D.O. levels, which can be attained by increased aeration rates by $O_2$ sparging, or by increasing the air pressure in the fermentor.

Acceptable carbon sources are known to those of skill in the art. For example, carbon can be provided to *C. cohnii* in the form of glucose. Other heterotrophs can use other reduced carbon sources, a matter easily determined by those of skill in the art, and autotrophs utilize carbon dioxide. *C. cohnii* will also grow on other reduced, more complex, carbon sources. Typically, a fermentation is initiated with about 10–50 g/liter glucose. More glucose is added during the fermentation as required. Alternatively, from about 50 to 150 g, preferably 50 to 100 g glucose/liter initially can be added, thereby minimizing the frequency of future additions. The amount of carbon source provided to other organisms can readily be determined by those of skill in the art.

In addition to a reduced carbon source, a nitrogen source, such as yeast extract (YE), is provided to the medium. Commercially available yeast extract is acceptable. For example, DIFCO or MARCOR brand yeast extract can be used. The yeast extract is an organic nitrogen source also containing micronutrients. Other organic nitrogen sources easily can be determined by those of skill in the art. However, such compounds are generally more expensive than yeast extract. The use of variants capable of growing on urea or nitrates is within the scope of this invention. Typically, the fermentation is initiated with about 6–12 g YE/liter. More YE can be added as required. A typical fermentation run requires from about 8 to 15 g YE/liter over the course of the run. Accordingly, that amount of YE can be added initially with a reduced need for further additions. The precise amount can be determined by those of skill in the art. Generally, the ratio of glucose to YE is from about 2:1 to about 15:1.

The cultivation can be carried out at any life-sustaining temperature. Generally C. cohnii will grow at temperatures ranging from about 15° C. to 34° C. Preferably the temperature is maintained at about 20°–30° C. Strains which grow at higher temperatures are preferred, because they will have a faster doubling time, thereby reducing the fermentation time. Appropriate temperature ranges for other microorganisms are readily determined by those of skill in the art.

The cultivation can be carried out over a broad pH range, typically from about pH 5.0 to 9.0. Preferably, a pH range of from about 6.0 to about 7.0 is used for the growth phase. A base, such as KOH or NaOH, is used to adjust the media pH prior to inoculation. During the later stages of the fermentation, the culture medium tends to become alkaline. If desired, inorganic acid pH controls can be used to correct alkalinity during the growth phase.

Production of the single cell oil is induced in the dinoflagellates by the imposition of a stationary phase (i.e., by nitrogen depletion or a pH rise). YE deficiencies are caused by providing YE in a limiting amount such that the medium runs out of YE while available glucose remains. The present invention recognizes that it is the carbon source to nitrogen source ratio which promotes the efficient production of the single cell oil. Using glucose and YE as exemplary, a preferred ratio of carbon source to nitrogen source is about 10–15 parts glucose to 1 part YE. Similar ratios for other carbon and nitrogen sources can be calculated by those of skill in the art.

After induction of oil production, the culture is grown for about 24 additional hours. During this period of oleosynthesis, the single cell oil containing DHA is being synthesized and visible oil droplets become apparent. Those of skill in the art can readily calculate the time of fermentation required to achieve the expected amount of cell biomass based upon the added amount of YE. When that time has passed, the culture is grown for an additional 24 hours and harvested. In general, the C. cohnii are cultivated for a time sufficient to produce single cell oil, usually from about 60 to about 90 hours, although this time is subject to variation.

From about 15 to 30% of the resultant biomass, using wild-type C. cohnii, comprises extractable oil. Strain selection can increase this percentage and such selection is within the scope of this invention. Preferably, the oil comprises greater than about 70% triglycerides having, in general, the following fatty acid composition.

15–20% myristic acid ($C_{14:0}$)
20–25% palmitic acid ($C_{16:0}$)
10–15% oleic acid ($C_{18:1}$)
30–40% DHA ($C_{22:6}$)
0–10% others (Other oil components including polar lipids, such as phosphatidyl choline, also may be enriched in DHA.) The crude oil is characterized by a yellow-orange color and is liquid at room temperature. Desirably, the oil contains at least about 20% DHA by weight and most preferably at least about 35% DHA by weight.

The organisms are harvested by conventional means, known to those of skill in the art, such as centrifugation, flocculation or filtration, and can be processed immediately or dried for future processing. In either event, the oil can be extracted readily with an effective amount of solvent. Suitable solvents can be determined by those of skill in the art. However, preferred solvents include pure hexane and supercritical fluids, such as supercritical $CO_2$.

Extraction techniques using supercritical fluids are known to those of skill in the art and described in McHugh et al., *Supercritical Fluid Extraction*, Butterworth, 1986. If the extraction solvent is hexane, a suitable ratio of hexane to dry biomass is about 4 liters of hexane per kilogram of dry biomass. The hexane preferably is mixed with the biomass in a stirred reaction vessel at a temperature of about 20°–50° C. for about 2 hours. After mixing, the biomass is filtered and separated from the hexane containing the oil. Alternatively, a wet biomass paste (30–35% solids) can be extracted directly with more polar solvents, such as ethanol, isopropanol or hexane/isopropanol mixtures. The residual biomass, i.e. the single cell edible oil extracted biomass of the microorganisms, such as C. cohnii, can be used as an animal feed, containing as it does about 35–40% protein, 8–10% ash and 45–50% carbohydrates. Because of this high protein content and the elevated levels of DHA, the whole biomass paste can be used for aquaculture (e.g., shrimp, oysters, fish) feed.

The solvent then is removed from the oil by distillation techniques known to those of skill in the art. Conventional oilseed processing equipment is suitable to perform the filtering, separation and distillation. Additional processing steps, known to those of skill in the art, can be performed if required or desirable for a particular application. These steps also will be similar to those involved in conventional vegetable oil processing and allow the separation of DHA-enriched polar lipid fractions.

Isotopically labeled single cell oils, including labeled DHA, can be easily obtained in sufficient quantities to permit research into the metabolic pathways of DHA by the method of this invention. When $^{13}$C-glucose or $^{14}$C-glucose is provided as the reduced carbon substrate, labeled DHA results.

The present invention also includes food products, such as infant formulas and baby foods, as well as dietary supplements, which contain the single-cell oil containing DHA of the present invention. While those of skill in the art have recognized that infant formulas containing DHA are desirable, the prior art infant formulas contained DHA from fish oil, with its attendant unpleasant tastes and organoleptic characteristics. Furthermore, fish oil supplementation of infant formula includes the addition of eicosapentaenoic acid (EPA), an omega-3-fatty acid known to possess anticoagulant activity and possibly responsible for reduction of arachidonic acid biosynthesis. Such an activity is not desirable in infant formula or baby food and the single cell oil described herein contains no significant quantity of EPA. Food products, such as infant formula, containing the single cell oil of the present invention do not have the unpleasant organoleptic characteristics of fish oil. The food products thus are more readily accepted by infants and adults alike. Preferably the infant formula of the present invention contains about 0.05% by weight of single cell oil containing DHA. The baby food of the present invention, having a more solid constitution, preferably contains about 0.5% by weight of single cell oil containing DHA. In both instances, most preferably, the oil contains at least about 35% DHA.

The present invention includes pharmaceutical products including single cell oil containing DHA. Preferably the products contain at least about 35% DHA. Exemplary of such pharmaceutical products is one suitable for use in providing total parenteral nutrition (TPN) to infants or adults. Additionally, dietary supplements containing the single cell oil are encompassed. Preferably, such supplements are in the form of gelatin capsules encapsulating said oil and may be appropriate for pregnant women or breast feeding mothers. This especially may be true for such women who are vegetarians and do not get sufficient amounts of DHA in their diets.

The present invention also includes single cell oil containing DHA. Preferably the single cell oil contains at least about 20% by weight DHA. Most preferably the oil contains at least about 35% by weight DHA.

The present invention having been generally described, reference is had to the following non-limiting specific examples.

EXAMPLE 1

Into a 30-liter working volume STF was loaded a medium of one half strength artificial seawater. Six liters of IO were combined with 18 liters of tap water. The fermentor containing the medium was sterilized and cooled to 28° C. Four hundred ml of concentrated YE (455 g/l), 900 ml of glucose syrup (400 g/l) and one liter of inoculum from a seed fermentor containing about $2 \times 10^7$ cells/ml or a biomass of 20 g/liter (yielding a final concentration of about $7 \times 10^6$ cells/ml or a biomass of about 700 mg/liter), were added to the medium. Agitation was set at 120 cm/sec tip speed and aeration was set at 1 VVM (30 liters per minute). Additional glucose syrup (900 ml) was added after 30 hours and another 4.2 liters over the next 42 hours. Thus 6 liters of glucose syrup were added in total. Concentrated YE solution (400 ml) was added at hour 6 and another 1.2 liters were added over the next 48 hours until a total of 2.0 liters had been added. To maintain the D.O. at greater than 20%, at 24 hours the agitation tip speed was increased to 150 cm/sec and at 48 hours to 160 cm/sec. At 72 hours, the tip speed was increased to 200 cm/sec and the culture was permitted to grow for an additional time sufficient to convert the final charge of glucose into cellular oil. The culturing conditions are depicted graphically in FIG. 1. The culture was then harvested by centrifugation with the cell pellet retained. The harvested pellet of cells was frozen and dried (lyophilized) to about a 4% moisture content. Hexane (2.8 liters) was added to the dried biomass and stirred in a glass kettle for 1.5 hours at 50° C. A rotary evaporator was used to remove the hexane, producing about 175 g of crude DHA-containing oil.

EXAMPLE 2

Figure 2:
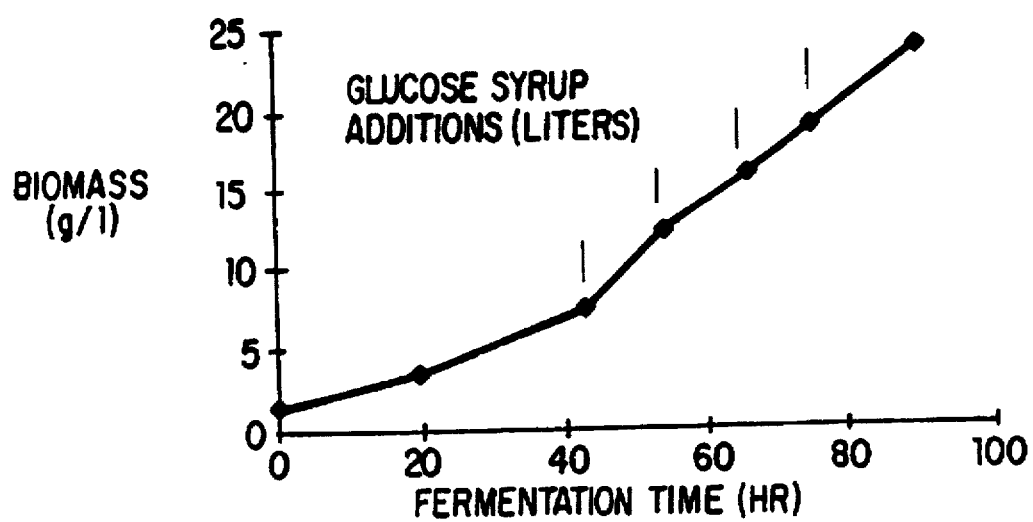

Into a 350-liter working volume STF was loaded a medium of one half strength artificial seawater made by combining 4.3 kg. of I.O.® with 230 liters of tap water. The fermenter containing the medium was sterilized and cooled to 28° C. 6.8 liters of concentrated YE (400 g/l), 12.5 liters of glucose syrup (400 g/l) and 30 liters of C. cohnii inoculum from a seed fermenter ($10^6$ cells/ml or a biomass density of about 1.3 g/liter) were added to the medium. Agitation was set at 73 cm/sec tip speed and aeration was set at 1 VVM (280 liters per minute). Additional glucose syrup (12 liters) was added after about 44 hours and another 43 liters over the next 32 hours. Thus, 67.5 liters of glucose syrup were added in total. The glucose additions and the cell growth are depicted graphically in FIG. 2.

To maintain the D.O. at greater than 20%, at 44 hours the agitation tip speed was increased to 175 cm/sec and at 55 hours to 225 cm/sec. At 76 hours, the tip speed was decreased to 150 cm/sec and the culture was permitted to grow for an additional time sufficient to convert the final charge of glucose into cellular oil. The culture then was harvested. The harvested cells were dried to about a 4% moisture content. Hexane was added to the dried biomass and stirred in a glass kettle for 2 hours at 25° C. A rotary evaporator was used to remove the hexane, producing about 700 g of crude DHA-containing oil.

EXAMPLE 3

Figure 3:
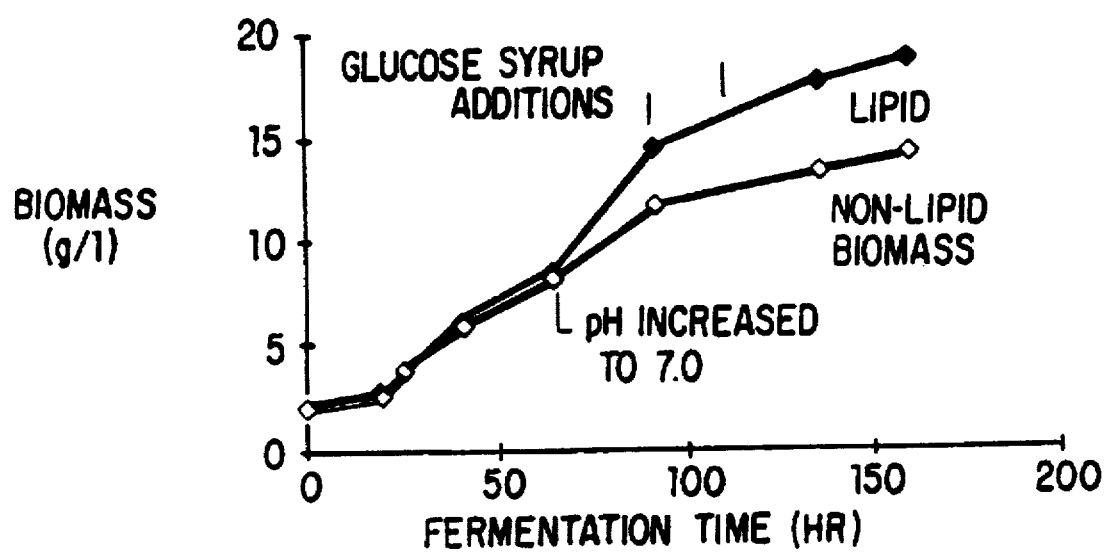

Into a 30-liter working volume STF was loaded a medium of full strength artificial seawater made by combining 565 g of I.O.® with 15 liters of tap water. The fermenter containing the medium was sterilized and cooled to 28° C. Four hundred ml of concentrated YE (400 g/l), 1.9 liters of glucose syrup (400 g/l) and 1 liter of C. cohnii inoculum from a seed fermenter ($10^6$ cells/ml or a biomass of about 2.0 g/liter) were added to the medium. Agitation was set at 80 cm/sec tip speed and aeration was set at 1 VVM (20 liters per minute). Additional glucose syrup (1.5 l) was added after 94 hours and another 1.1 liters at 116 hours. Thus 4.5 liters of glucose syrup were added in total. To maintain the D.O. at greater than 20%, at 52 hours the agitation tip speed was increased to 160 cm/sec. At 66 hours, stationary phase was induced and in order to accomplish this, the pH was spiked with 4N KOH to 7.0 and the agitation tip speed was not further increased for the duration of the run. As shown in FIG. 3, the culture was permitted to grow for an additional time sufficient to convert the final charge of glucose into cellular oil. The culture then was harvested. The harvested cells were dried to about a 4% moisture content. Hexane was added to the dried biomass and stirred in a glass kettle for 1.5 hours at 50° C. A rotary evaporator was used to remove the hexane, producing about 65 g of crude DHA-containing oil.

We claim:

1. A biomass consisting essentially of cells of microorganisms, said cells being produced by
    cultivating heterotrophic microalgae of the class Dinophyceae in a fermentor to achieve a cell density of at least about 10 grams biomass per liter of nutrient solution, by maintaining in the fermentor a dissolved oxygen level of at least about 10% of air saturation, inducing, by imposition of a stationary phase with a limiting nitrogen source in the nutrient solution, production of a single cell oil containing at least 20% docosahexaenoic acid (DHA) in the triglyceride form at a concentration of at least about 1.5 grams per liter of nutrient solution, and
    harvesting said biomass from said fermentor.

2. The biomass of claim 1, wherein the microalgae is of the genus Crypthecodinium.

3. The biomass of claim 2, wherein said microalgae is C. cohnii.

4. The biomass according to claim 1, wherein the microorganism is cultivated to a cell density of at least about 20 g/liter of nutrient solution.

5. The biomass according to claim 1, wherein imposition of the stationary phase is a consequence of limiting nitrogen source in the nutrient medium.

6. The biomass according to claim 1, wherein the single cell edible oil contains no significant quantity of eicosapentaenoic acid (EPA).

7. The biomass according to claim 1, wherein the biomass comprises at least about 15% single cell oil by weight.

8. An aquaculture feed comprising biomass according to claim 1.

9. The aquaculture feed of claim 8, wherein the aquaculture comprises shrimp, oysters or fish.

10. A biomass consisting essentially of cells of *Crypthecodinium cohnii*, said cells being produced by cultivating said cells in an aerobic fermentor to achieve a cell density of a least 10 grams biomass per liter of nutrient solution, by maintaining in the fermentor a dissolved oxygen level of at least about 10% of air saturation, and inducing, by imposition of a stationary phase with a limiting nitrogen source in the nutrient solution or with an increase in pH, production of a single cell oil which contains at least 20% docosahexaenoic acid (DHA) in the triglyceride form at a concentration of at least about 1.5 grams per liter of nutrient solution, and harvesting said biomass from said fermentor.

\* \* \* \* \*